(12) United States Patent
Harty

(10) Patent No.: US 8,119,618 B2
(45) Date of Patent: *Feb. 21, 2012

(54) COMPOSITIONS AND METHODS FOR THE TREATMENT OF INFLAMMATORY DISEASES

(75) Inventor: Richard F. Harty, Oklahoma City, OK (US)

(73) Assignee: The Board of Regents of the University of Oklahoma, Norman, OK (US)

(*) Notice: Subject to any disclaimer, the term of this patent is extended or adjusted under 35 U.S.C. 154(b) by 191 days.

This patent is subject to a terminal disclaimer.

(21) Appl. No.: 12/402,378

(22) Filed: Mar. 11, 2009

(65) Prior Publication Data

US 2010/0063012 A1 Mar. 11, 2010

Related U.S. Application Data

(63) Continuation of application No. 11/347,113, filed on Feb. 2, 2006, now Pat. No. 7,691,832, which is a continuation of application No. 11/023,812, filed on Dec. 28, 2004, now Pat. No. 7,417,037.

(60) Provisional application No. 60/537,766, filed on Jan. 20, 2004.

(51) Int. Cl.
*A61K 31/30* (2006.01)
*A01N 43/00* (2006.01)
*A01N 37/36* (2006.01)

(52) U.S. Cl. ........ 514/159; 514/160; 514/161; 514/162; 514/163; 514/164; 514/165; 514/166

(58) Field of Classification Search .......... 514/159–166, 514/474
See application file for complete search history.

(56) References Cited

U.S. PATENT DOCUMENTS

| 4,664,256 A | 5/1987 | Halskov |
| 5,668,117 A | 9/1997 | Shapiro |
| 6,444,221 B1 | 9/2002 | Shapiro |
| 2008/0081035 A1 | 4/2008 | Parmely et al. |

FOREIGN PATENT DOCUMENTS

| EP | 0398207 A1 | 11/1990 |
| WO | 95/31194 | 11/1995 |

OTHER PUBLICATIONS

Siddiqui, A. et al., "Antioxidant Therapy with N-Acetylcysteine Plus Mesalamine Accelerates Mucosal Healing in a Rodent Model of Colitis", Digestive Diseases and Sciences, vol. 51, No. 4 (Apr. 2006), pp. 698-705.
Bantel, H. et al., "Mesalazine Inhibits Activation of Transcription Factor NF-kappaB in Inflamed Mucosa of Patients With Ulcerative Colitis", The American Journal of Gastroenterology, vol. 95, No. 12, 2000, pp. 3452-3457.
Seril, D.N., et al. "Inhibition of Chronic Ulcerative Colitis-Associated Colorectal Adenocarcinoma Development in a Murine Model by N-Acetylcysteine", Carcinogenesis, Vo.. 23, No. 6, 2002, pp. 993-1001.
Farinati, et al., "Effects of N-Acetyl-L-Cysteine in Patients with Chronic Atrophic Gastritis and Nonulcer Dyspepsia: A Phase III Pilot Study", Current Therapeutic Research, vol. 58, No. 10, 1997, 724-733.
Guijarro, L. et al., "Supplemental N-Acetyl-L-Cysteine Improves the Efficacy of Mesalazine in the Treatment of Mild to Moderate Ulcerative Colitis. Randomized, Placebo-Controlled, Pilot Study", Gastroenterology, vol. 126, No. 4, Suppl. 2, Abstract No. T1295, Apr. 2004.
Myers, R.H.and Montgomery, D.C., "Response Surface Methodology" 2nd Edition, 2002, Wiley-Interscience, New York, NY.

*Primary Examiner* — Sreeni Padmanabhan
*Assistant Examiner* — Renee Claytor
(74) *Attorney, Agent, or Firm* — Sam K. Tahmassebi; TechLaw LLP

(57) ABSTRACT

Inflammatory bowel diseases are represented by two idiopathic disorders, which include ulcerative colitis and Crohn's disease. Ulcerative colitis is restricted to the colon and involves uncertain and inflammation of the lining (mucosa) of the large intestine. Crohn's disease, on the other hand, can involve the mucosa of the small and/or large intestine and may involve deeper layers of the bowel wall. The present invention is a combination of 5-aminosalicylic acid and one or more antioxidants (e.g., N-acetylcysteine) for treating such inflammatory bowel diseases.

19 Claims, 6 Drawing Sheets

COMPOSITIONS AND METHODS FOR THE TREATMENT OF INFLAMMATORY DISEASES

RELATED APPLICATIONS

This application is a continuation of U.S. application Ser. No. 11/347,113, filed on Feb. 2, 2006, by Richard F. Harty, and entitled "COMPOSITIONS AND METHODS OF TREATMENT FOR INFLAMMATORY DISEASES," now U.S. Pat. No. 7,691,832, issued on Apr. 6, 2010, which is a continuation of U.S. application Ser. No. 11/023,812, filed on Dec. 28, 2004, now U.S. Pat. No. 7,417,037, issued on Aug. 26, 2008, by Richard F. Harty, and entitled "COMPOSITIONS AND METHODS OF TREATMENT FOR INFLAMMATORY DISEASES," which in turn claims the benefit under 35 U.S.C. 119(e) of U.S. Provisional Application Ser. No. 60/537,766, filed Jan. 20, 2004, the entire disclosure of all of which is hereby expressly incorporated by reference herein.

BACKGROUND

Inflammatory bowel diseases (IBDs) including ulcerative colitis and Crohn's disease, are complex diseases that are thought to result from over activation of the immune system directed at luminal antigens of the gastrointestinal tract (12). In the early 1940's it was observed that sulfasalazine, formed by the chemical union of the antibiotic sulfapyridine and 5-aminosalicylic acid (5-ASA; also referred to as mesalamine) by an azo bond, had a beneficial effect in patients with colitis (29). Subsequent clinical studies over the next two decades established that sulfasalazine had efficacy in the treatment of inflammatory bowel disease (30, 31). Additional studies were directed to determine the chemical kinetics of sulfasalazine when administered orally and to determine mechanisms of action (32-34). Approximate 75% of sulfasalazine reaches the colon unchanged. Within the colon the azo bond is split by bacterial enzyme action into metabolites, 5-ASA and sulfapyridine. Following azo bond reduction, most of the sulfapyridine is absorbed from the colon whereas only 20% of 5-ASA is absorbed. The majority of 5-ASA remains in the colon and is recovered in the feces primarily as free 5-ASA.

Postulated mechanisms for the presumed beneficial action of sulfasalazine in the treatment of colitis initially included inhibition of prostaglandin synthesis and inhibition of the lipoxygenase pathway in inflammatory cells such as neutrophils (35,36). Ensuing investigations have established additional therapeutic mechanisms whereby 5-ASA promotes healing and reduces inflammation in IBD (2, 37, 38). These include: free radical scavengers, inhibit T-cell proliferation, inhibit presentation of antigen to T-cells, inhibit adhesion of macrophages and granulocytes, decrease production of interleukins (ILs) and down regulation of the transcription factor, NF-κB, activity. Despite the utility of sulfasalazine for patients with inflammatory bowel disease, experience has shown that up to one third of patients cannot tolerate this medication and manifest one or more side effects of variable severity. These side effects are related directly to systemic absorption of sulfapyridine. Because of sulfasalazine-related side effects, investigators have examined 5-ASA as a single agent for the treatment of inflammatory bowel disease. There have been several formulations of 5-ASA designed to inhibit proximal intestinal absorption and delivery of this compound to areas of active inflammation (39). Several formulations of 5-ASA have been studied and those currently most popular include coated forms of 5-ASA that are released in a pH-sensitive manner to the distal ileum and colon. Examples of such agents include Asacol™ (Proctor and Gamble) and Pentasa™ (Shire US inc.). Furthermore, 5-ASA preparation for rectal delivery has included the development of suppositories and enemas containing 5-ASA as the active agent. Examples include Rowasa™ rectal suspension enema (Solvay Pharmaceuticals) and 5-ASA suppositories such as Canasa™ (Axcan Scandiapharm). Thus, a number of oral or rectally delivered 5-ASA agents are presently available for the treatment of mild to moderate inflammatory bowel disease.

Recent investigations into the etiological triad of genetic: environmental: immune factors have expanded our knowledge of these individual components and their potential interactions. Pathogenetic models of IBD envision initiating events, possible microbiologicals, arising from the gut lumen that converts immune tolerance to a sustained hyperactive state with elaboration and amplification of cellular and humoral mediators. Immunocyte derived injurious and proinflammatory substances cause tissue injury and destruction. These substances include prostaglandins, reactive oxygen metabolites, nitric oxide, leukotrienes, proteases and matrix metalloproteinases (3). The role of reactive oxygen species (ROS) and nitric oxide (NO) have been examined in experimental models of IBD (4, 5). Pharmacological and genetic manipulation of oxygen free radical and NO generation have been shown to ameliorate experimental colitis induced by luminal administered trinitrobenzene sulfonic acid (TNBS) and dextran sulfate sodium (DSS) (5-10).

Although several experimental strategies have been employed that suggest the importance of enhanced production of superoxide and nitric oxide in the pathogenesis of IBD, inconsistent results have the issue unresolved. For example, the beneficial effect of superoxide dismutase (SOD) treatment in experimental models of colitis has been reported while SOD treatment in humans with IBD has shown limited benefit (40). Similarly, the inhibitors of inducible nitric oxide synthase (iNOS) have yielded mixed results in various experimental models of IBD (6-8, 27). The antioxidants N-acetylcysteine (NAC) and phenyl N-tert-butylnitrone (PBN) when used alone have been shown to be effective in protection against TNBS-induced colitis in rat (9) and DSS-induced colitis in mice, (10) respectfully. Furthermore, recent studies suggest a dominant role of iNOS-derived NO in a murine model of colitis (5). Antioxidant therapy has also been shown to suppress colonic iNOS activity and to decrease colonic NF-κB DNA-binding activity in experimental animals (10). Nuclear factor-κB, NF-κB is a family of transcription factors known to regulate a variety of genes controlling the inflammatory process and regulating programmed cell death (41).

Thus, there exists extensive experimental support for the notion that reactive oxygen molecules and nitric oxide may contribute to the pathogenesis of mucosal injury in inflammatory bowel disease. Furthermore, experimental evidence also provides support for the concept that inhibition of nitric oxide species and NO generation exert favorable effects on mucosal healing and the inflammatory process in several well-defined models of chemically induced colitis. However, there continues to be a need in the field for a more effective treatment of inflammatory bowel diseases and other conditions related to inflammation. It is to this need that the present invention is directed.

SUMMARY OF THE INVENTION

Disclosed herein are methods of treating an inflammatory bowel disease comprising administering a composition comprising 5-aminosalicylic acid and N-acetylcysteine to a mammal or contacting a colonic cell of the mammal with the said composition. Also disclosed are methods of reducing cytokine gene expression or reducing myeloperoxidase activity in colonic tissue of a mammal, the method comprising administering a composition comprising 5-aminosalicylic acid and N-acetylcysteine to a mammal or contacting a colonic cell of the mammal with the said composition.

DESCRIPTION OF THE INVENTION

The present invention contemplates use of 5-ASA (mesalamine) plus an antioxidant either together as separate molecular entities or when coupled chemically, to provide an enhanced therapeutic or prophylactic effect against inflammatory bowel diseases in mammals. The combination of mesalamine plus an antioxidant in a mammal model of colitis promotes healing and reduces inflammation to a significantly greater degree than either agent when used alone. The present invention provides an improved anti-inflammatory effectiveness of 5-ASA for use in the treatment of inflammatory bowel disease by the addition of an antioxidant. Use of the presently claimed compositions result in a reduction in the need for additional anti-inflammatory agents, such as prednisone and Imuran in the treatment of inflammatory disease (thereby providing a significant cost benefit and reduction in drug-induced toxicity.). Furthermore, the present invention can serve as a model for additional pharmacological approaches to other inflammatory and, possibly, neoplastic conditions within the gastrointestinal tract.

As shown below experiments were performed to examine the ability of an antioxidant (NAC) and 5-ASA, when administered separately or in combination to the distal colon, to affect mucosal healing and repair following colitis chemically-induced by TNBS or DSS.

Materials and Methods

Experimental Animals

Male Sprague Dawley rats (200-250 grams) were housed in cages containing contact bedding. Rats were deprived of food for 24 hrs prior to the induction of colitis, but were allowed free access to water throughout the experiment. Institutional approval for experimental protocols was provided by the research and animal care committees of the research services at the Oklahoma City Veterans Administration Medical Center.

Induction of Colitis by TNBS Treatment

Figure 1:
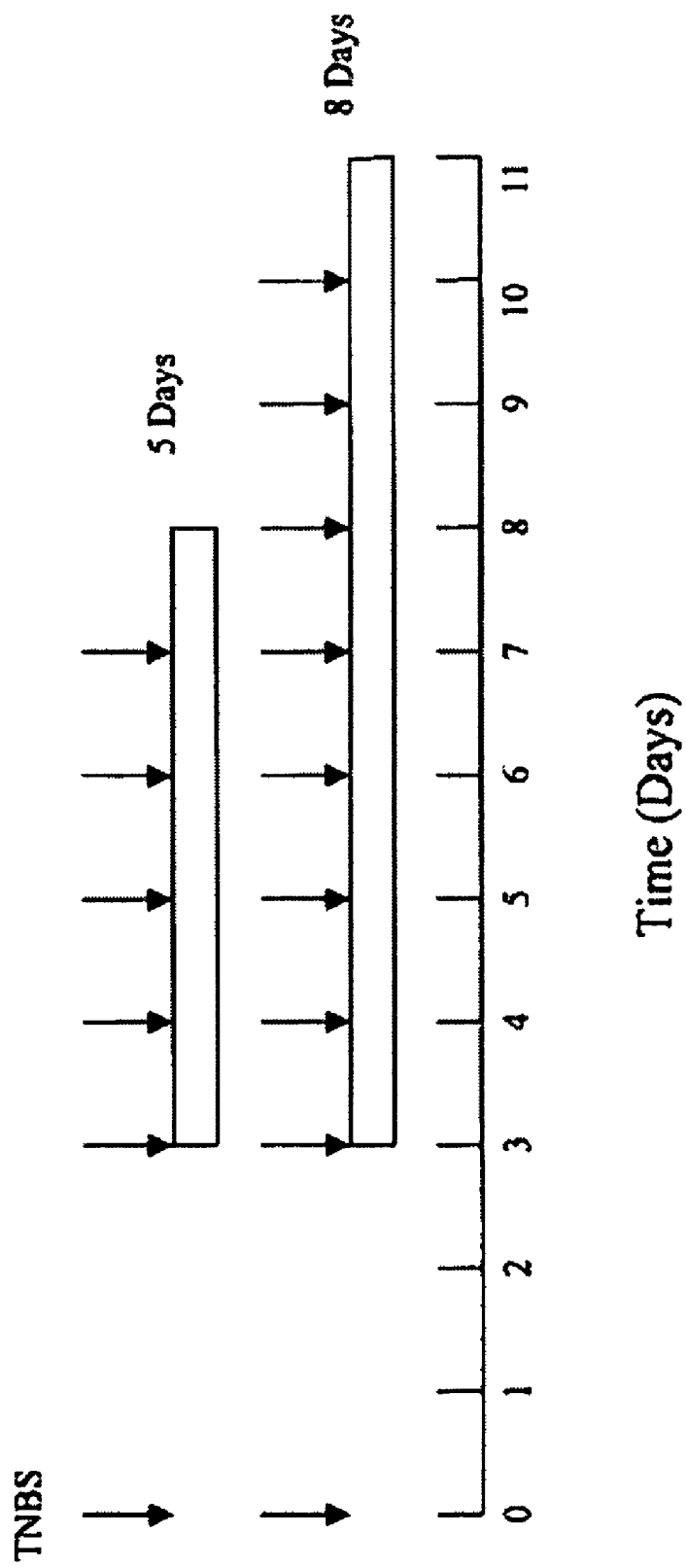
FIG. 1: Experimental Design: Colitis was induced at day 0 by rectal administration of TNBS. Three days after TNBS dosing rats received daily intraluminal therapy per rectum for either 5 or 8 days. Four treatment protocols were employed and included: (A) 5-ASA (100 mg/kg), (B) NAC (40 mM), (C) a combination of 5-ASA (100 mg/kg) and NAC (40 mM), and (D) a saline control.

Following a 24 hr fast, rats were lightly anesthetized using isoflurane followed by insertion of a polyethylene catheter into the anus. The tip of the catheter was advanced 8 cm proximal from the anus and a single dose of TNBS (Sigma, St. Louis, Mo.), dissolved in 50% ethanol, was injected through the cannula (15 mg dissolved in a 0.6 ml volume of 50% ethanol) to induce colitis. Following the administration of TNBS the animals were maintained in a head-down position for approximately 60 seconds to prevent leakage of the infusate. After 72 hrs, rats dosed initially with TNBS were randomly assigned to one of four treatment groups to receive daily intracolonic therapy in a manner similar to that used for TNBS administration. The groups were: A.) 5-aminosalicylic acid (5-ASA) (100 mg/kg) B.) N-acetylcysteine (NAC) (40 mM) plus 5-ASA (100 mg/kg) C.) NAC (40 mM), or D.) saline. An additional group of rats (Group E) served as control and received saline per rectum on day 0 and at subsequent intervals that corresponded to treatment protocols. Rats were treated for either 5 or 8 days and then sacrificed by cervical dislocation. FIG. 1 illustrates the design of these experiments.

Induction of Colitis by DSS Treatment

Colitis was induced by oral administration of a 4% solution of DSS (dextran sulfate sodium) in drinking water for 4 days. Experimental groups were randomized to include group 1 control, group 2-5 received DSS in drinking water and groups 3-5 were further randomized to receive daily intracolonic treatment with 5-ASA (100 mg/kg) plus NAC (40 mM), group 3; 5-ASA alone, group 4; and NAC constituted group 5. Animals received treatment for 4 days. Macroscopic indices of colonic injury were scored and tabulated. Histological features that were examined included epithelial damage and mucosal ulceration. Additional measures included determination of serum C-reactive protein (CRP) levels and cytokine gene expression in colonic tissues performed by ribonuclease protection assay (RPA).

Macroscopic Assessment of Colitis

Upon sacrifice, the distal 8 cm of the colon was removed, opened by a longitudinal incision and rinsed with phosphate buffered saline to remove fecal material. Macroscopic assessment of colitis was carried out by an independent observer who was unaware of the treatment groups. The criterial and scale of grading are listed in Table 1. Inflammation was present if the mucosa was erythematous. Ulceration of the mucosa was defined as a distinct break or interruption of the mucosa. Once macroscopic damage was assessed full thickness colonic tissue samples were taken from the inflamed areas and either processed for histology or snap frozen in liquid nitrogen for subsequent cytokine measurement and determination of myeloperoxidase (MPO) activity.

TABLE 1

Macroscopic Scoring of colitis

| Macroscopic Injury | Score |
|---|---|
| Normal | 0 |
| One area of inflammation No ulcer | 1 |
| No inflammation One ulcer | 2 |
| One area of inflammation One or two ulcers | 3 |
| One area of inflammation More than 2 ulcers | 4 |
| Two areas of inflammation More than 2 ulcers | 5 |
| Ulceration >2 cm | 6 |

Histological Assessment of Colitis

Colonic tissue samples taken from the initial segment were immersed in 10% phosphate buffered formalin and subsequently embedded in paraffin. Sections of 3 micron thickness were cut and stained with hematoxylin and eosin. The slides were then evaluated by a pathologist for epithelial damage, architectural changes, mononuclear infiltration, polymorphonuclear leukocyte (PMN) infiltration and ulceration. The individual microscopic features of colitis were graded according to criteria noted in Table 2. In addition to scoring individual features of colitis, an aggregate score of colitis was tabulated by adding together individual scores, thus, providing a global assessment of colitis.

TABLE 2

Histological Scoring of Colitis

| Epithilial Damage | 0 | Normal |
| | 1 | Focal Mucosal injury |
| | 2 | Extensive mucosal injury |
| Architectural Damage | 0 | Normal |
| | 1 | Moderately disturbed |
| | 2 | Severely disturbed |
| Mononuclear Infiltration | 0 | Normal |
| | 1 | Moderate increase |
| | 2 | Severe increase |
| PMN Infiltration | 0 | Normal |
| | 1 | Present in surface epithelium |
| | 2 | Cryptitis |
| | 3 | Crypt abscesses |
| Ulcerations | 0 | None |
| | 1 | 1%-33% ulcerated |
| | 2 | 34%-66% ulcerated |
| | 3 | 67% + ulcerated |

Myeloperoxidase Activity

Myeloperoxidase activity was used as an indirect measure of the severity of colonic inflammation by PMNs. Whole thickness tissues taken following macroscopic assessment were weighed (100 mg) and immediately snap frozen in liquid nitrogen for storage at −80.degree. C. The tissues were then removed from storage at −80° C. and allowed to thaw on ice. Once thawed, 1 ml of hexadecyltrimethylamonium bromide (HTAB) (Sigma, St. Louis, Mo.) containing 50 mM $KH_2PO_4$ (Sigma, St. Louis, Mo.) and 0.1M $Na_2HPO_4$ (Sigma, St. Louis, Mo.) was added per 100 mg tissue for homogenization. Homogenates then underwent a series of four freeze/thaw cycles before finally being centrifuged at 12,000×g for 10 minutes at 4° C. The supernatant was collected for measurement of MPO activity. Horseradish peroxidase (Sigma, St. Louis, Mo.) was used as a standard; stock solution of 0.5 mg/ml. Tetramethylbenzidine (TMB) (Sigma, St. Louis, Mo.) was used as the substrate for carrying out the reaction. At the time of assay 25 μl of standard and sample were added to appropriately labeled tubes. TMB was added at a volume of 250 μl to initiate the reaction and 0.1 M $H_2SO_4$ (250 μl) was added after 10 minutes to terminate the reaction. The absorbance changes were read at 450 nm and recorded. Results were expressed as ng/ml/g of tissue.

Ribonuclease Protection Assay (RPA)

Following the manufacturer's protocol, 1 ml of TRI Reagent (Sigma, St. Louis, Mo.) is used per 100 mg of tissue. The frozen tissue is placed into the TRI Reagent and immediately homogenized using a tissue macerator. The homogenates are transferred to microcentrifuge tubes and 0.2 ml of chloroform is added per ml of TRI Reagent used. The samples are shaken thoroughly and allowed to sit at room temp for 3 min. Samples were then centrifuged at 12000×g for 15 min at 40° C. After centrifugation, the upper aqueous phase was transferred to a new tube and 9.5 ml of 2-propanol is added to precipitate the RNA. After sitting at room temp for 10 min. the samples are centrifuged at 12000×g for 15 min. The supernatants are discarded and the pellets are washed in 70% ethanol followed by centrifugation at 12000×g for 5 min. The ethanol was removed and the pellets are dissolved in 50 μl of DEPC treated water per sample. Quantitation is performed by spectrophotometry at 260 nm and 280 nm.

RPA analysis was performed with RiboQuant™ multiprobe RNase protection assay system (BD Biosciences-Pharmingen, San Diego, Calif.). To 20 μg of total RNA in 8 μl of hybridization buffer and 2 μl of $^{32}$P-labeled in vitro transcribed RNA probes were added. The probes were transcribed from the multiprobe template set rCK-1 which as a panel of probes against IL-1a, IL-1b, IL-3, IL-5, IL-10, IL-2, TNFα, TNBβ, GAPDH genes. Probes were prepared according to the manufactures protocol. The RNA samples containing labeled probes were incubated briefly at 90° C., slowly cooled to 56° C. and hybridized overnight at that temperature. The samples were then slowly cooled to 30° C. Thereafter, a mixture of RNases A and T1 was added to digest single-stranded RNA leaving the double-stranded RNA formed by the probes annealing to their cognate mRNAs intact. Following proteinase K digestion and phenol-chloroform extraction, the undigested double-stranded RNA was precipitated with ammonium acetate and ethanol. After centrifugation at 14000×g for 20 min., the pellets are washed with 90% ethanol and recentrifuged. The ethanol was removed and the pellets were dissolved in 5 μl of formamide loading dye. The double-stranded RNAs were resolved on a 5% polyacrylamide/urea gel run in TBE buffer. After electrophoresis, the gel was dried at 80° C. under vacuum and then exposed to a PhosphorImager screen overnight. Detection and quantitation of the resolved bands on the gel were performed on a Storm PhosphorImager™ system (Amersham Biosciences, Piscataway, N.J.).

Statistical Significance

All values in the figures and text are expressed as means±standard error of the mean (SEM). The statistical significance of any difference among groups was analyzed using Student's two-tailed t test for equal and unequal variance observations. P values of <0.05 were considered to be statistically significant.

Results

Macroscopic Findings

8 Days After TNBS; 5-Day Treatment

Figure 2:
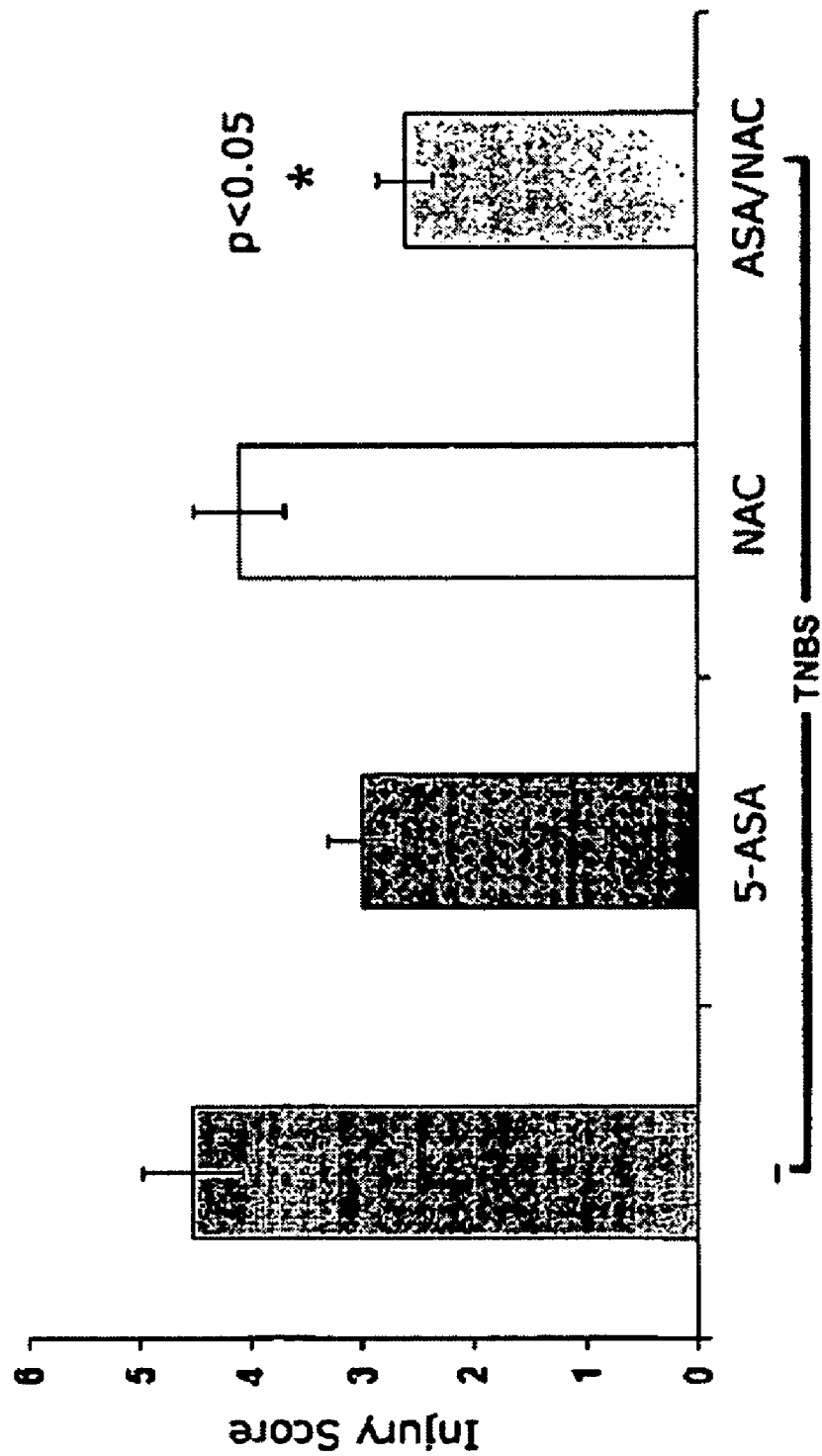
FIG. 2: Macroscopic grading of inflammation and injury 8 days after intracolonic administration of TNBS. Macroscopic grading (0-6) 8 days after TNBS revealed moderately severe inflammation and ulceration: score 4.5±0.5. Therapy with the NAC/5-ASA combination for 5d was the only intervention that significantly reduced macroscopic injury: score 2.6±0.7. These results are representative of 4 different experiments done at different times with 5 animals per group per each experiment. * denotes $p<0.05$ vs TNBS.

The macroscopic injury observed at 8 days after rats received TNBS was 4.5±0.5. This value indicated that the distal 8 cm of colon contained more than 2 discrete ulcers in an area of inflammation (FIG. 2). In contrast, combination therapy with the NAC plus 5-ASA combination acted synergistically to cause a significant reduction in macroscopic injury as reflected by an injury score of 2.6±0.7; p<0.05. Monotherapy with either NAC or 5-ASA alone caused reduction in macroscopic injury (4.1±0.6 and 3.0±0.7, respectively) but these values did not achieve significance when compared to TNBS alone.

11 Days After TNBS; 8-Day Treatment

Figure 3:
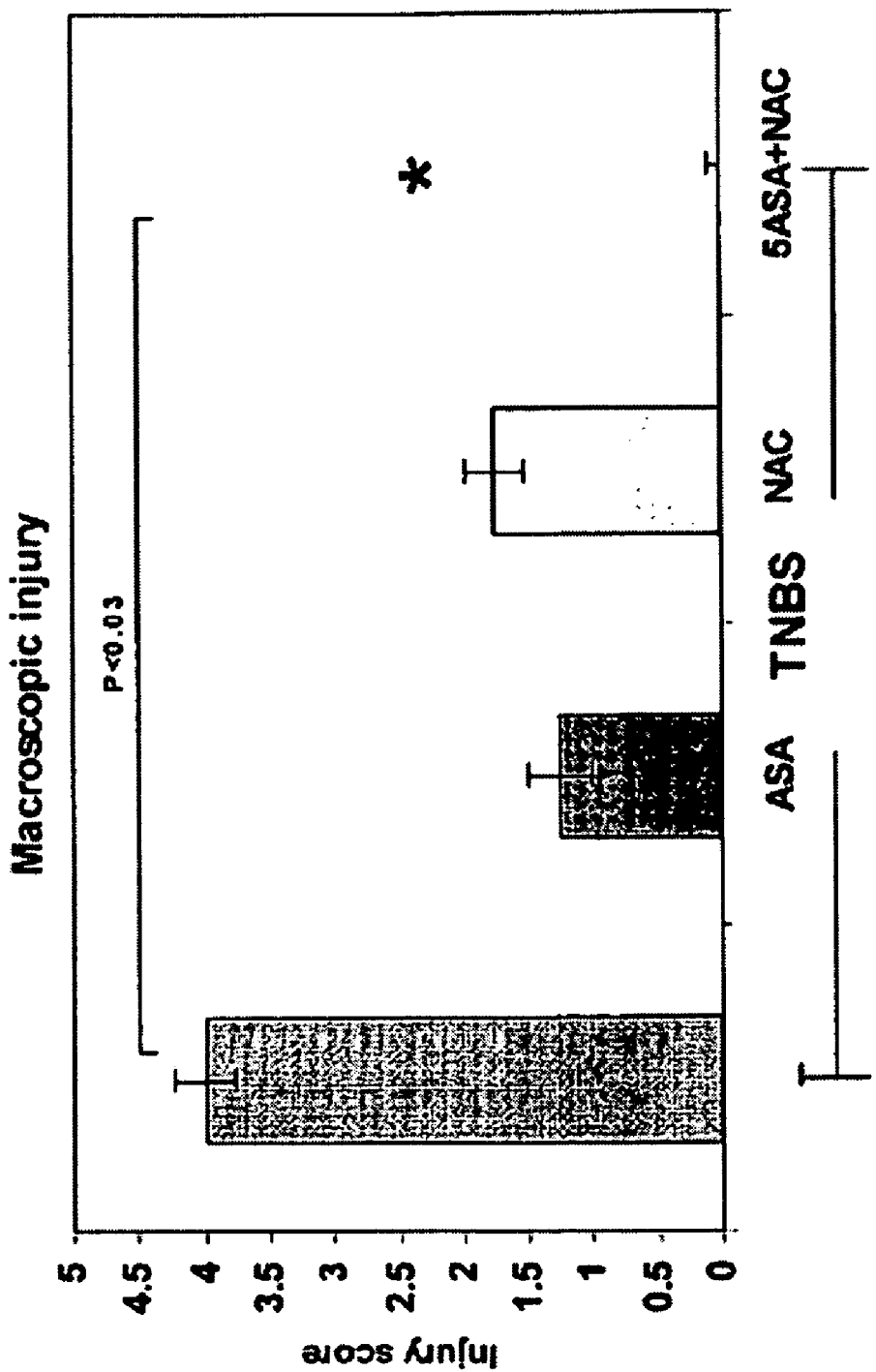
FIG. 3: Macroscopic injury score 11 days after TNBS and 8 days of treatment with 5-ASA alone, NAC alone and the NAC and 5-ASA combination.

Visual evidence of colitis 11 days after TNBS was scored at 4.1±0.2 (FIG. 3). Animal treated with the NAC plus 5-ASA combination for 8 days showed no evidence of mucosal inflammation on ulceration. The colonic mucosa in these animals appeared normal. Monotherapy with either NAC or 5-ASA alone showed mild inflammation and macroscopic injury scores were 1.2±0.2 and 1.8±0.2 respectively.

Microscopic Findings

8 Days After TNBS; 5-Day Treatment

Figure 4:
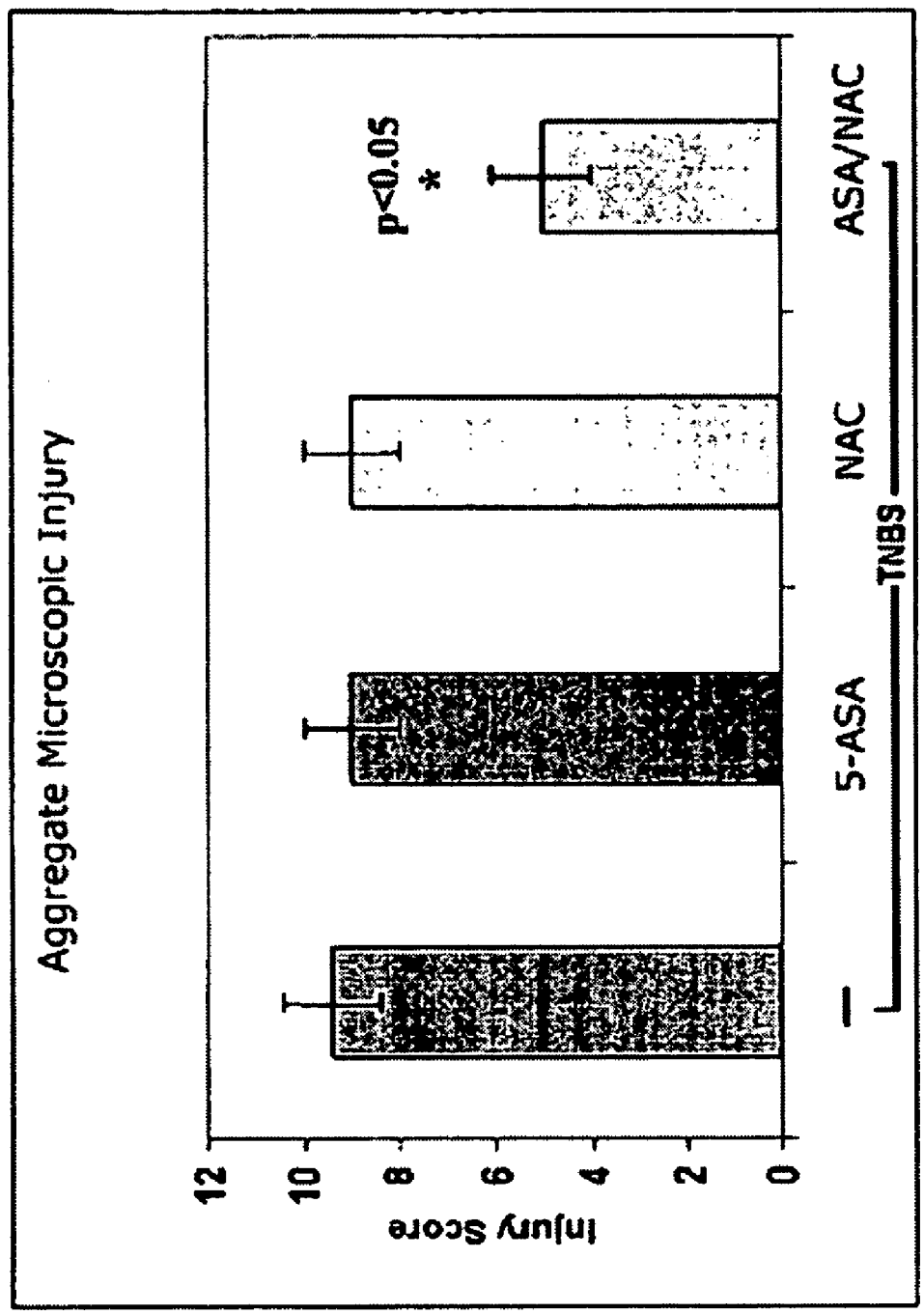
FIG. 4: Microscopic grading of inflammation and injury 8 days after intracolonic administration of TNBS. Microscopically, TNBS affected significantly each parameter of injury and inflammation as reflected by a cumulative microscopic injury score (0-15) of 9.4±1.0 $p<0.001$. The NAC/5-ASA combination significantly reduced the cumulative microscopic injury: score 5.0±1.2 $p<0.001$. Single agent therapy with either NAC alone or 5-ASA alone did not significantly decrease microscopic injury: NAC 9.0±1.8, and 5-ASA 9.0±0.9. These results are representative of 4 different experiments done at different times with 5 animals per group per experiment. *denotes $p<0.05$ vs TNBS.

The cumulative or aggregate microscopic colitis injury score for rats examined 8 days after TNBS was 9.4±1.0 which represented moderately severe colitis (FIG. 4). Individual therapy for 5 days with either 5-ASA or NAC alone did not alter the aggregate injury score: 9.0±0.9 and 9.0±1.8, respectively. Therapy with the NAC plus 5-ASA combination, however, caused significant reduction (−44%) in cumulative colitis injury and resulted in a score of 5.0±1.2, P<0.02. Subset analysis of individual histological features, when compared to TNBS alone, indicated that therapy with the NAC plus 5-ASA combination acted synergistically to significantly reduce the degree of epithelial damage, the extent of mucosal ulceration and the amount of mononuclear cell infiltration.

11 Days After TNBS; 8-Day Treatment

Figure 5:
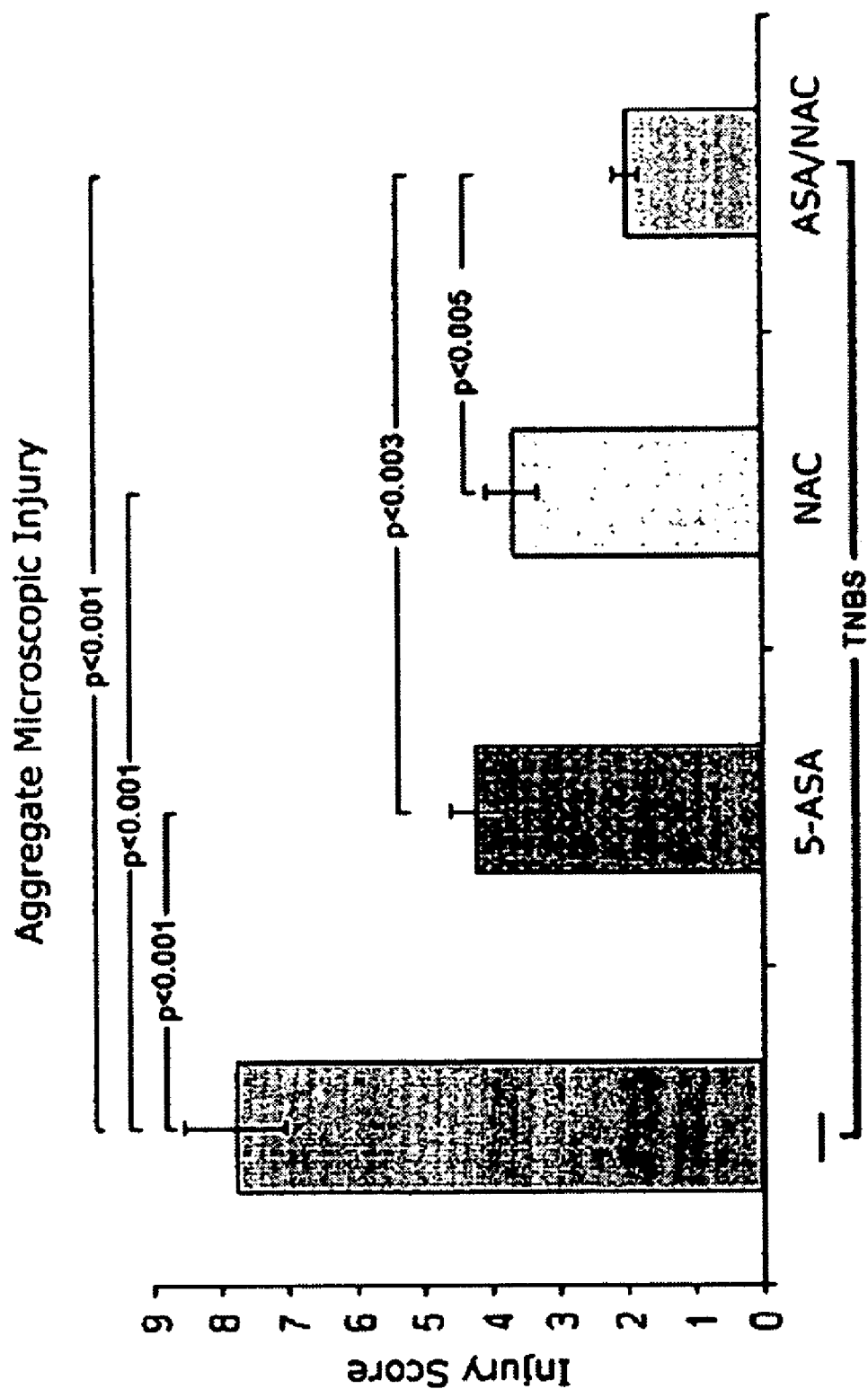
FIG. 5: Combination therapy with the NAC/5-ASA combination for 8 days reduced significantly the aggregate microscopic injury score by 75%. Therapy was initiated 3 days after induction of colitis by TNBS. Furthermore, single agent therapy with 5-ASA alone and NAC alone also significantly decreased histological measures of injury by 46 and 53%, respectively. The degree of histologic healing with the NAC/5-ASA combination was significantly greater than that observed with either 5-ASA or NAC alone.

Eleven days post TNBS the indices of microscopic colitis were reduced slightly but not significantly from aggregate scores recorded at 8 days after TNBS: 7.0±0.9 vs 9.5±1.0; P>0.1. In contrast to the histological results after 5 days of treatment each of the intraluminal therapies for 8 days caused significant reduction in global measures of colitis (FIG. 5). 5-ASA and NAC each when administered alone caused comparable decrease in aggregate injury of 46 and 53%, respectively. Combination therapy with the NAC plus 5-ASA combination caused a 75% reduction in cumulative colitis injury score: 1.8±0.5 vs 7.0±0.9 TNBS alone; P<0.001. Furthermore, comparisons between monotherapies with either 5-ASA or NAC alone and combination therapy indicated that the NAC plus 5-ASA combination acted synergistically to produce a significantly greater degree of healing than either NAC or 5-ASA alone.

Myeloperoxidase Activity

Figure 6:
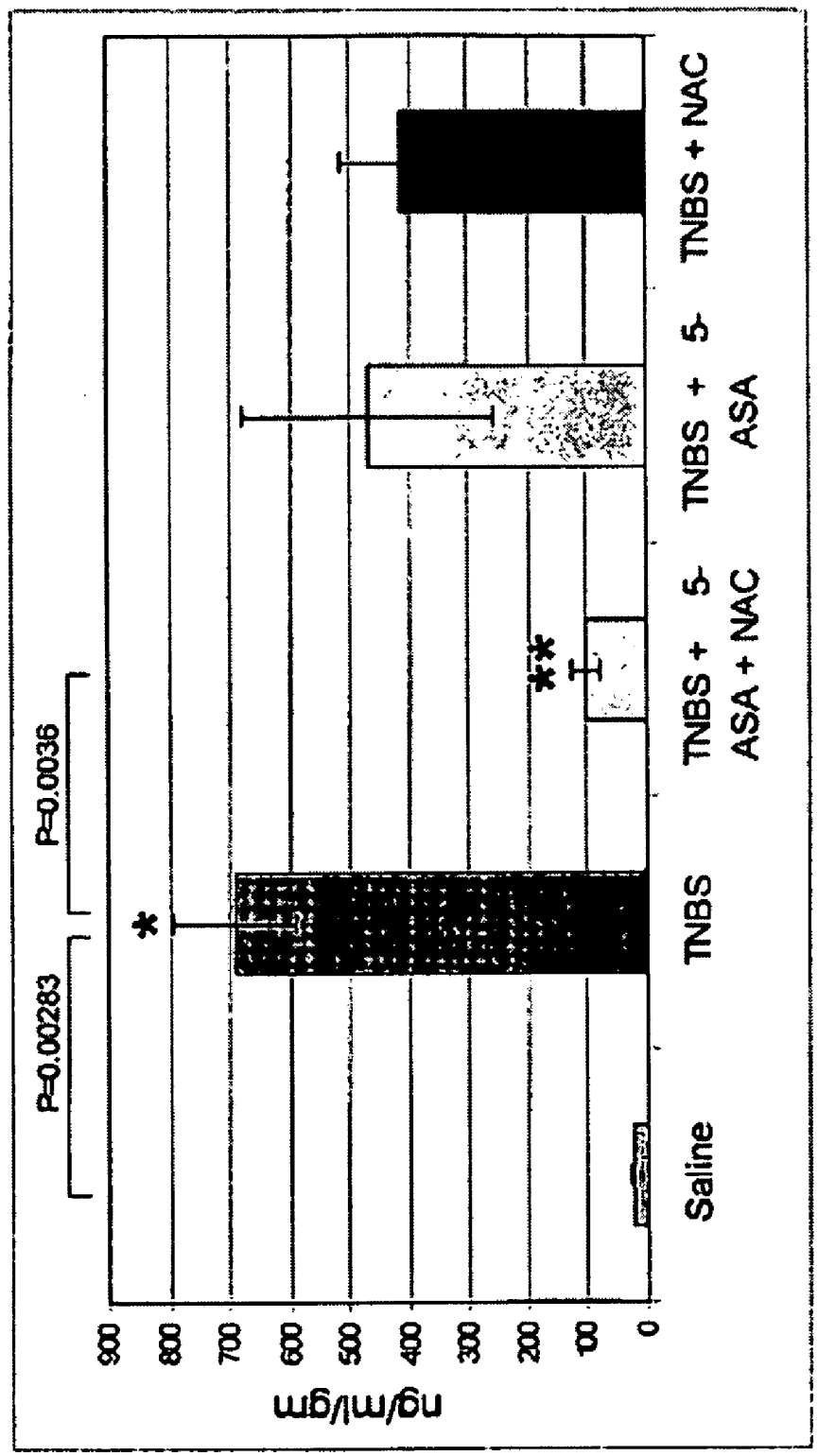
FIG. 6: Myeloperoxidase activity in colon tissue 11 days after TNBS and 8 days of treatment with 5-ASA alone, NAC alone and the NAC plus 5-ASA combination. Results represent the mean±SEM of 4-6 rats per condition.

MPO activity in colonic tissue 11 days after TNBS treatment was elevated greater than 25 fold above values derived from saline treated rats (FIG. 6). In contrast, the NAC plus 5-ASA combination treatment for 8 days reduced MPO activity by 85% to 100.9±12.9 ng/g (P<0.004 vs TNBS 690.2±101.5 ng/g). MPO activity was also reduced by both NAC and 5-ASA alone to levels that were 40% and 32% below TNBS values but these differences did not achieve statistical significance.

Inflammatory Cytokine Expression

Cytokine gene expression in colonic tissues indicate that elevations in interleukins (IL 1a, IL 1b, IL-4 and IL-6) and TNF α that were induced by TNBS after 11 days were inhibited significantly by 8 day treatment with the NAC plus 5-ASA combination (Table 3). Treatments with either NAC or 5-ASA alone did not significantly suppress levels of cytokine expression induced by TNBS.

TABLE 3

Cytokine gene expression in rat colon

| cytokine | Treatment Group | Relative O.D units Mean ± SEM |
|---|---|---|
| IL-1A | Saline | 0.54 ± 0.07 |
| | TNBS only | 1.97 ± 0.3 |
| | TNBS + 5ASA = NAC | 0.70 ± 0.08** |
| | TNBS + 5ASA | 1.33 ± 0.18 |
| | TNBS + NAC | 1.28 ± 0.16 |
| IL-1B | Saline | 2.25 ± 0.37 |
| | TNBS only | 11.77 + 1.7 |
| | TNBS + 5ASA + NAC | 6.03 ± 0.62** |
| | TNBS + 5ASA | 11.49 + 2.54 |
| | TNBS + NAC | 11.88 + 1.0 |
| IL-4 | Saline | 0.27 ± 0.06 |
| | TNBS only | 1.76 ± 0.42 |
| | TNBS + 5ASA + NAC | 0.82 ± 0.12** |
| | TNBS + 5ASA | 1.40 ± 0.25 |
| | TNBS + NAC | 1.20 ± 0.26 |
| IL-6 | Saline | 0.18 ± 0.03 |
| | TNBS only | 1.21 ± 0.37 |
| | TNBS + 5ASA + NAC | 0.46 ± 0.06** |
| | TNBS + 5ASA | 0.79 ± 0.22 |
| | TNBS + NAC | 0.76 ± 0.14 |
| TNF-α | Saline | 0.41 ± 0.06 |
| | TNBS only | 1.51 ± 0.13 |
| | TNBS + 5ASA + NAC | 0.7 ± 0.15** |
| | TNBS + 5ASA | 1.25 ± 0.12 |
| | TNBS + NAC | 1.04 ± 0.017 |

**denotes a P value<0.05 vs TNBS alone
Data represent the Mean ± SEM of 6-10 observations per condition Results of the TNBS experiments of the present study indicate that intraluminal administration of the NAC plus 5-ASA combination to the distal colon of rats with TNBS colitis act synergistically to cause a significant reduction in colonic inflammation and ulceration and acceleration of mucosal healing when compared to either agent used alone. Furthermore, combination therapy with the NAC plus 5-ASA combination caused significantly greater inhibition of myeloperoxidase activity and proinflammatory cytokine gene expression in colons of TNBS treated animals than either NAC or 5-ASA alone. Duration of treatment was a determinant in the effectiveness of antioxidant and anti-inflammatory agents on healing of chemically induced colitis. The NAC plus 5-ASA combination was the only dosing regimen that resulted in significant improvement in both macroscopic and microscopic measures of colitis after a five day treatment. In contrast, eight day treatment with NAC alone, 5-ASA alone or the NAC plus 5-ASA combination resulted in significant improvement in histological features of colitis. Treatment with the NAC plus 5-ASA combination, however, caused greater improvement in mucosal injury, inflammation and epithelial regeneration than NAC or 5-ASA alone. Data derived from these studies indicate that intraluminal therapy with the antioxidant NAC plus 5-ASA combination is superior to either agent alone in the treatment of TNBS colitis and that dual therapy has a synergistic effect in reducing inflammation and promoting mucosal repair.

Colitis induced by intracolonic instillation of TNBS manifests many of the histological and clinical features of colonic inflammatory bowel disease (11). This model of colonic ulceration and transmural inflammation of the mucosa (12) has been employed to study the pathogenesis of colonic inflammation and to investigate potential treatments of IBD. In this latter regard previous reports have shown that both 5-ASA and NAC, when administered singly by intracolonic route to rats, (9, 13) exerted an anti-inflammatory effect on TNBS colitis. Furthermore, the antioxidant NAC was observed to increase colonic glutathione stores which were associated with a reciprocal decrease in the extent of mucosal injury (9). In support of these observations and the role of ROS generation in TNBS colitis Loguercio et al reported that glutathione supplementation improved oxidative damage in TNBS colitis (14).

Antioxidants, such as NAC, and 5-ASA possess the ability to scavenge oxygen free radicals, inhibit inducible NO formation and to down regulate nuclear factor κB (NF-κB) activity (9, 10, 15-17). Furthermore, antioxidants, such as phenyl N-tert-butylnitrone, and 5-ASA have been shown to inhibit cytokine production, including tumor necrosis factor TNFα, and to retard adhesion module expression and B-cell mediated antibody production (10, 18-20) in experimented models of colitis. Separately and together these agents can, thus, be envisioned to moderate immunocyte (T cell) mediated cytokine elaboration, neutrophil generation of ROS and NO, prostaglandin release and to facilitate an environment for unopposed cellular and growth factor-mediated tissue repair. These results show that treatment with the NAC plus 5-ASA combination cause marked improvement in indices of colitis and, furthermore, demonstrate prominent features of epithelial repair, and mucosal architectural and glandular restoration. These data combined with the near normalization of MPO activity and marked reduction in cytokine (ILa, ILb, IL6) expression indicate that therapy with the NAC plus 5-ASA combination exerts a significantly greater anti-inflammatory and reparative effect in TNBS colitis than either 5-ASA or NAC when used alone.

Results in the DSS experiments demonstrated that DSS under these experimental conditions produced mild to moderate colitis. The aggregate microscopic injury score for DSS treated animals was 5.5±2.0; maximal score 12. Monotherapy with either 5-ASA or NAC alone caused slight reduction in aggregate scores to 4.1±0.9 and 4.0±1.1, respectively. These values were not significantly different from DSS alone. In contrast, combination therapy with the NAC plus 5-ASA combination reduced global or aggregate histological injury score by 67% to 1.8±0.8. Furthermore, the NAC plus 5-ASA combination caused significant improvement in epithelial damage when compared to DSS alone. DSS colitis was associated with elevated CRP values of 7.0±0.6 mg/ml. CPR levels were reduced substantially by concurrent therapy with NAC plus 5-ASA and values were 1.0±0.3 mg/ml. Similar reductions in CRP levels were observed with either 5-ASA or NAC alone. DSS treatment caused marked elevation in cytokine gene expression for IL 1a and IL 1b and these values represented a 6.8 and 12.1 fold increase, respectively, in gene expression of these cytokines when measured above control values.

NAC and 5-ASA, alone or in combination, substantially reduced DSS-induced IL 1a and IL1b gene expression by 55-90% to levels that approximated control values. Conclusions from these data indicate that intraluminal therapy with the NAC plus 5-ASA combination caused significant amelioration of mucosal injury induced by DSS. Combination treatment with the NAC plus 5-ASA combination results were associated with substantial reduction in serum CRP levels and proinflammatory cytokine gene expression.

Current considerations of the pathogenesis of mucosal inflammation in IBD involve a number of steps from antigen presentation and processing by macrophages to amplification of T cell activation and differentiation and cytokine production (1). In addition, inflammatory cells, including granulocytes and mononuclear cells, are recruited to the mucosa in a highly coordinated fashion. Once present in the inflamed mucosa, tissue injury is enhanced by neutrophil production of reactive oxygen species such as superoxide and an increase in the expression of the inducible isoform of NO synthase (iNOS) (5). Mucosal healing is thought to occur, in part, by reduction in injurious and proinflammatory substances and, also, by local liberation of growth factors which facilitate cellular restitution and repair (2). Although several experimental approaches have been employed that suggest the importance of enhanced production of superoxide and nitric oxide in the pathogenesis of IBD, inconsistent results have this issue unresolved (5). The beneficial effect superoxide dismutase (SOD) treatment in experimental models of colitis (21-23) has shown limited effect in humans with IBD (24). In addition, iNOS inhibition has shown variable results in experimental models of IBD (25-27). However, recent studies using gene-targeted mice suggest a dominant role of iNOS-derived NO in a murine model of dextran sulfate sodium (DSS) colitis (5). The antioxidants NAC and phenyl N-tert butylnitrone have been shown to be effective in reducing the injurious consequences of TNBS colitis in rats (9) and DDS colitis in mice (10), respectively. Antioxidant therapy has also been demonstrated to suppress colonic iNOS activity and to decrease NF-κB DNA-binding activity in experimental colitis (10) and man (16).

In conclusion, our results showed that treatment of TNBS-induced colitis with the NAC plus 5-ASA combination was superior to either 5-ASA or NAC when used alone in reducing colonic inflammation and in promoting mucosal repair. In addition, combination therapy with the NAC plus 5-ASA combination acted synergistically to result in a significant reduction in MPO activity and proinflammatory cytokine gene expression.

Utility

The present invention provides a method for the treatment of a mammal subject (including humans) afflicted with inflammatory diseases, and in particular, inflammatory bowel diseases. The present invention has several advantages over current therapies. As demonstrated herein, combination therapy with 5-ASA plus an antioxidant is synergistically superior to either agent alone in controlling mucosal inflammation. It is envisioned that such combination therapy would be capable of being delivered by oral route, employing existing coating technologies, to sites of inflammation. In addition, such combination therapy would be amenable to local therapy in the distal colon and rectum by enema or suppository. Further description regarding deliver methods and dosing systems and protocols is discussed below.

The combination of at least two active anti-inflammatory agents into a single delivery system as described herein provides greater clinical efficacy, development of a new pharmacochemical strategy for treating mucosal inflammatory conditions, and a reduction in the need for other potentially toxic and expensive anti-inflammatory agents. The chemical coupling of 5-ASA to an antioxidant substance can provide a further pharmacological approach to the treatment of mucosal inflammatory conditions such as IBD.

The 5-ASA used in the composition of the present invention may be provided as the free acid, or as a pharmaceutically-acceptable salt or ester, for example as described in U.S. Pat. No. 5,013,727, the entirety of which is hereby expressly incorporated by reference herein.

Both 5-ASA and antioxidants such as NAC and phenyl N-tert-butylnitrone have relatively low profiles for toxicity. 5-ASA may be associated with allergic reactions to the medications and should be avoided in patients with aspirin sensitivity. As with any nonsteroidal agent there exists potential for hepatic and renal toxicity. N-acetylcysteine or Mucomyst™ has had a wide experience in man for the treatment of acetaminophen hepatotoxicity. This agent has proven safe. Other antioxidants contemplated for use herein in conjunction with 5-ASA include other aminosalicylates including 4-aminosalicylic acid (4-ASA), and N-acetyl-5-aminosalicylic acid; other nonsteroidal anti-inflammatory drugs (NSAIDs) including those that inhibit cyclooxygenase I and/or II, such as sulindac, celecoxib and refacoxib; ascorbate; vitamin C; vitamin A; Vitamin E; beta-carotene; herbal agents such as milk thistle; selenium; iron in various ferric and ferrous formulations; phospholipase A2 inhibitors, e.g., carboxymethylcellulose-linked phosphatidylethanolamine; superoxide dismutase mimetics, such as Mn(II/III) tetrakis (1-methyl-4-peridyl) of NmTMPyP; melatonin; zolimid; rebamipide; and phenyl N-tert-butylnitrone (PBN); and combinations of any of the above.

While is it contemplated that applications of the invention would be principally of treating mucosal inflammatory conditions associated with inflammatory bowel diseases, such as ulcerative colitis, Crohn's disease and Behcet's disease, the invention would also have application to other disorders of the gastrointestinal tract such as radiation and infective enteritis, ischemic injury to the gastrointestinal tract, infectious, caustic agent-induced gastrointestinal injury, hemorrhagic rectal ulcer, ileum pouchitis, ischemic enteritis and drug-induced colitis, mucous colitis, pseudomembranous enterocolitis, non-specific colonic ulcers, collagenous colitis, cathartic colon, ulcerative proctitis, idiopathic diffuse ulcerative non-granulomatous enteritis, non-steroidal anti-inflammatory drug-induced inflammations, celiac sprue and the like. Furthermore, advances in our understanding of the pathogenesis of gastrointestinal malignancies suggest a role for prostaglandins generated by the cyclooxygenase enzymes to have a role in neoplasia. It has been well established that nonspecific and specific cyclooxygenase inhibitors can reduce the propensity to neoplasia and malignancy in experimental models and in human subjects. Full appreciation of the role of prostaglandins in the cyclooxygenase system in the pathogenesis of gastrointestinal malignancy is not complete. However, it is conceivable that therapies which combine inhibition prostaglandin synthesis through the cyclooxygenase enzymes and antioxidant therapies may have a beneficial role in preventing gastrointestinal malignancies such as colorectal cancer.

The term "inflammation" as used herein is meant to include reactions of both the specific and non-specific defense systems. A specific defense system reaction is a specific immune system reaction response to an antigen. Examples of a specific defense system reaction include the antibody response to antigens such as rubella virus, and delayed-type hypersensitivity response mediated by T-cells (as seen, for example, in individuals who test "positive" in the Mantaux test).

A non-specific defense system reaction is an inflammatory response mediated by leukocytes incapable of immunological memory. Such cells include granulocytes, macrophages, neutrophils, for example. Examples of a non-specific defense system reaction include the immediate swelling at the site of a bee sting, the reddening and cellular infiltrate induced at the site of a burn and the collection of PMN leukocytes at sites of bacterial infection (e.g., pulmonary infiltrates in bacterial pneumonias, pus formation in abscesses).

Although the invention is particularly suitable for cases of acute inflammation, it also has utility for chronic inflammation. Types of inflammation that can be treated with the present invention include diffuse inflammation, traumatic inflammation, immunosuppression, toxic inflammation, specific inflammation, reactive inflammation, parenchymatous inflammation, obliterative inflammation, interstitial inflammation, croupous inflammation, and focal inflammation.

A therapeutically effective amount of a composition of the present invention refers to an amount which is effective in controlling, treating or moderating the inflammatory response. The terms "controlling", "treating" or "moderating" are intended to refer to all processes wherein there may be a slowing, interrupting, arresting, or stopping of the progression of the disease and does not necessarily indicate a total elimination of all disease symptoms.

The term "therapeutically effective amount" is further meant to define an amount resulting in the improvement of any parameters or clinical symptoms characteristic of the inflammatory response. The actual dose will be different for the various specific molecules, and will vary with the patient's overall condition, the seriousness of the symptoms, and counter indications.

As used herein, the term "subject" or "patient" refers to a warm blooded animal such as a mammal which is afflicted with a particular inflammatory disease state. It is understood that guinea pigs, dogs, cats, rats, mice, horses, cattle, sheep, goats, pigs, llamas, and humans are among the examples of animals within the scope of the meaning of the term.

A therapeutically effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease or condition involved; the degree of or involvement or the severity of the disease or condition; the response of the individual subject; the particular compound administered; the mode of administration; the bioavailability characteristic of the preparation administered; the dose regimen selected; the use of concomitant medication; and other relevant circumstances.

A therapeutically effective amount of the compositions of the present invention will generally contain sufficient active ingredient (i.e., the antioxidant and 5-ASA) to deliver from about 0.1 µg/kg to about 6000 mg/kg (weight of active ingredient/body weight of patient). Preferably, the composition will deliver at least 1.0 µg/kg to 1000 mg/kg, and more preferably at least 1 mg/kg to 100 mg/kg, although each dose of the composition may be more or less than these amounts. For example, the daily dose for an adult may be in the range of about 10 mg to 300 mg/kg, preferably in the range of about 20 mg to 300 mg/kg, especially in the range of 50 mg/kg to 200 mg/kg. Also see U.S. Pat. No. 5,013,727 which is incorporated by reference herein.

Practice of the method of the present invention comprises administering to a subject a therapeutically effective amount of the composition described herein, in any suitable systemic or local formulation, in an amount effective to deliver the dosages listed above. The dosage can be administered on a one-time basis, or (for example) from one to five times per day or once or twice per week, or continuously via a venous drip, depending on the desired therapeutic effect.

As noted, preferred amounts and modes of administration are able to be determined by one skilled in the art. One skilled in the art of preparing formulations can readily select the proper form and mode of administration depending upon the particular characteristics of the compound selected, the disease state to be treated, the stage of the disease, and other relevant circumstances using formulation technology known in the art, described, for example, in Remington's Pharmaceutical Sciences, latest edition, Mack Publishing Co.

Pharmaceutical compositions can be manufactured utilizing techniques known in the art. Typically the therapeutically effective amount of the compound will be admixed with a pharmaceutically acceptable carrier.

The compounds or compositions of the present invention may be administered by a variety of routes, for example, orally, intrarectally or parenterally (i.e., subcutaneously, intravenously, intramuscularly, intraperitoneally, or intratracheally).

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of this invention can be tabletted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, and buffers as are known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

As noted above, the compositions can also include an appropriate carrier. For topical use, any of the conventional excipients may be added to formulate the active ingredients into a lotion, ointment, powder, cream, spray, or aerosol. For surgical implantation, the active ingredients may be combined with any of the well-known biodegradable and bioerodible carriers, such as polylactic acid and collagen formulations. Such materials may be in the form of solid implants, sutures, sponges, wound dressings, and the like. In any event, for local use of the materials, the active ingredients usually be present in the carrier or excipient in a weight ratio of from about 1:1000 to 1:20,000, but are not limited to ratios within this range. Preparation of compositions for local use are detailed in Remington's Pharmaceutical Sciences, latest edition, (Mack Publishing).

Additional pharmaceutical methods may be employed to control the duration of action. Increased half-life and controlled release preparations may be achieved through the use of polymers to conjugate, complex with, or absorb the composition described herein. The controlled delivery and/or increased half-life may be achieved by selecting appropriate macromolecules (for example, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide, and the appropriate concentration of macromolecules as well as the methods of incorporation, in order to control release.

Another possible method useful in controlling the duration of action by controlled release preparations and half-life is incorporation of the glycosulfopeptide molecule or its functional derivatives into particles of a polymeric material such as polyesters, polyamides, polyamino acids, hydrogels, poly (lactic acid), ethylene vinylacetate copolymers, copolymer micelles of, for example, PEG and poly(l -aspartamide).

Alternatively, it is possible to entrap the compostions in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in the latest edition of Remington's Pharmaceutical Sciences.

U.S. Pat. No. 4,789,734 describe methods for encapsulating compositions in liposomes and is hereby expressly incorporated by reference herein. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", Drug Carriers in Biology and Medicine, pp. 287-341 (Academic Press, 1979). Microspheres formed of polymers or proteins are well known to those skilled in the art, and can be tailored for passage through the gastrointestinal tract directly into the blood stream. Alternatively, the agents can be incorporated and the microspheres, or composite of microspheres, implanted for slow release over a period of time, ranging from days to months. See, for example, U.S. Pat. Nos. 4,906,474; 4,925,673; and 3,625,214 which are expressly incorporated by reference herein.

When the composition is to be used as an injectable material, it can be formulated into a conventional injectable carrier. Suitable carriers include biocompatible and pharmaceutically acceptable phosphate buffered saline solutions, which are preferably isotonic.

For reconstitution of a lyophilized product in accordance with this invention, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field.

The pharmaceutical composition may also be in the form of an aqueous solution containing many of the same substances as described above for the reconstitution of a lyophilized product.

The compounds can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

As mentioned above, the compounds of the invention may be incorporated into pharmaceutical preparations which may be used for therapeutic purposes. However, the term "pharmaceutical preparation" is intended in a broader sense herein to include preparations containing a 5-ASA/antioxidant composition in accordance with this invention, used not only for therapeutic purposes but also for reagent or diagnostic purposes as known in the art, or for tissue culture. The pharmaceutical preparation intended for therapeutic use should contain a "pharmaceutically acceptable" or "therapeutically effective amount" of the composition, i.e., that amount necessary for preventative or curative health measures. If the pharmaceutical preparation is to be employed as a reagent or diagnostic, then it should contain reagent or diagnostic amounts of a 5-ASA/antioxidant combination.

All references, patents and patent applications cited herein are hereby incorporated herein in their entirety by reference.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings.

CITED REFERENCES

1. Konstantions A, Papadakis K A, Targan S R. Current theories on the causes of inflammatory bowel disease. Gastroenterol CLin North Am 28: 283-296; 1999

2. Sands B E. Novel therapies for inflammatory bowel disease.
Gastroenterol Clin North Am 18: 323-351; 1999

3. Sands B E. Crohn's Disease. In: Gastrointestinal and Liver Disease. Eds. M Feldman, L S Friedman, M H Sleisenger. Saunders; New York, 2002 pp 2005-2038.

4. Grisham M B. Oxidants and free radicals in inflammatory bowel disease. Lancet B44: 859-861; 1994.

5. Krieglstein C F, Cerwinka W H, Laroux S, et al. Regulation of murine intestinal inflammation by reactive metabolites of oxygen and nitrogen: Divergent roles of superoxide and nitric oxide. J Exp Med 194: 1207-1218; 2001.

6. Rachmilewitz D, Karmeli F, Okon E, et al. Experimental colitis is ameliorated by inhibition of nitric oxide synthase activity. Gut 37: 247-255; 1995.

7. Yoshida Y, Iwai A, Itoh M, et al. Role of inducible nitric oxide synthase in dextran sulfate sodium-induced colitis. Aliment Pharmacol Ther 14: 26-32; 2000.

8. McCafferty D M, Miampamba M, Shiota E. Role of inducible nitric oxide synthase in Trinitrobenzene sulphonic acid induced colitis in mice. Gut 45: 199-209; 1999.

9. Ardite E, Sans M, Panes], et al. Replenishment of glutathione levels improves mucosal function in experimental acute colitis. Lab Invest 80: 735-744; 2000.

10. Naito Y. Takagi T, Ishikawa T, et al. .alpha. Phenyl-N-tert-Butylnitrone provides protection from dextran sulfate sodium-induced colitis in mice. Antioxidants and Redox Signaling 4: 195-206; 2002.

11. Morris G P, Beck P L, Herridge M S, et al. Hapten-induced model of chronic inflammation and ulceration in the rat colon. Gastroenterology 1989; 96: 795-803.

12. Wallace J I. Release of platelet-activating factor (PAF) and accelerated healing induced by a PAF antagonist in an animal model of chronic colitis. Can I Physiol Pharmacol 1988; 66: 422-425.

13. Galvez J, Gamido M, Rodríguez-Cabezas M E, et al. The intestinal anti-inflammatory activity of UR-12746S on reactivated experimental colitis is mediated through down regulation of cytokine production. Inflamm Bowel Dis 2003; 9: 363-371.

14. Loguercio C, D'Argenio G, Delle Cave M, et al. Glutathione supplementation improves oxidative damage in experimental colitis. Dig Liver Dis 2003; 35: 635-641.

15. Grisham M B. A radical approach to treating inflammation. Trends in Pharmacological Sci 2000; 21: 119-120.

16. Bantel H, Berg C, Vieth M, et al. Mesalamine inhibits activation of transcription factor NF-kB in inflamed mucosa of patients with ulcerative colitis. Am J Gastroenterol 2000; 95: 3452-3457.

17. MacDermott R P. Progress in understanding the mechanism of action of 5-aminosalicylicacid. Am J Gastroenterol 2000; 95: 3343-3345.

18. Imai F, Suzuki T, Ishibashi T, et al. Effect of sulfasalazine on B cell. Clin Exp Rheumalol 1991; 9: 256-264.

19. Barrera P, Boerbooms A M, Van Der Putte L B A, et al. Effects of antirheumatic agents on cytokines. Sewin Arthritis Rheum 1996; 25: 234-253.

20. Green field S M, Hambhin A S, Shakor Z S, et al. Inhibition of leukocyte adhesion molecule upregulation by tumor necrosis factor .alpha.: a novel mechanism of action of sulfasalazine. Gut 1993; 34: 252-256.

21. Keshavarzian, A, Morgan G, Sedghi S, Gordon J H, and Doria M. 1990. Role of reactive oxygen metabolites in experimental colitis. Gut 31: 786-790.

22. Miller M J, McNeill H, Mullane K M, Caravella S J, and Clark D A. 1988. SOD prevents damage and attenuates eicosanoid release in a rabbit model of necrotizing enterocolitis. Am J Physiol 255:G556-G565.

23. Clark D A, Formabaio D M, McNeill H, Mullane K M, Carvella S J and Miller M J. 1988. Contribution of oxygen-derived free radicals to experimental necrotizing enterocolitis. Am J. Physiol. 130:537-542.

24. Rachmilewitz D, Karmeli F, Okon E, et al. Experimental colitis is ameliorated by inhibition of nitric oxide synthase activity. Gut 1995; 37: 247-255.

25. Yoshida Y, Iwai A, Itoh K, Tanaka M, Kato S, Hokari R, Miyahara T, Koyama H, Miura S, and Kobayashi M. 2000. Role of inducible nitric oxide synthase in dextran sulfate sodium-induced colitis. Ailment Pharmacol Ther 14: 26-32.

26. McCafferty D M, Miampamba M, Shiota E, Sharkey K A, and Kubes P. 1999. Role of inducible nitric oxide synthase in trinitrobenzene sulphonic acid induced colitis in mice. Gut 45: 864-873.

27. Zingarelli B, Szabo C, and Salzman A L. 1999. Reduced oxidative and nitrosative damage in murine experimental colitis in the absence of inducible nitric oxide synthase. Gut 45: 199-209.

28. Kubes P, and McCafferty D M. 2000. Nitric oxide and intestinal inflammation. Am J Med 109: 150-158.

41. Barnes P. J., Karin M. Nuclear factor-κB: a pivotal transcription factor in chronic inflammatory disease. N Engl J Med 336: 1066-1071; 1997.

29. Svarty N. Salazopyrin. A new sulfanilamide preparation. Acta Med Scand 1 10: 577 1942.

30. Dick A. P., Grayson M. J., Carpenter R. G., et al. Controlled trial of sulphosalazine in treatment of ulcerative colitis. Gut 5:437-442; 1964.

31. Misiewitcz J. J., Leonard-Jones J. E., Connell A. M., et al. Controlled trial of sulphosalazine in maintenance therapy for ulcerative colitis. Lancet 1:185-188; 1979.

32. Das K. M., Chowdhury J. R., Zapp B., et al. Small bowel absorption of sulphasalazine and its hepatic metabolism in human beings, cats and rats. Gastroenterology 77: 28-284; 1979.

33. Peppercorn M. A., Goldman P. The role of intestinal bacteria in the metabolism of salicylazosulphopyridine. J Pharmacol Exp Ther 181: 555-562; 1972.

34. Schroder H., Campbell D. E. Absorption, metabolism and excretion of salicylazosulphopyridine in man. Clin Pharmocol Ther 13: 539-552; 1972.

35. Sharon P., Ligumsky M., Rachmilewitz D., et al. Role of prostaglandins in ulcerative colitis: Enhanced production during active disease and inhibition by sulfasalazine. Gastroenterology 75: 638-640; 1975.

36. Ronne I. A., Nielson O. H., Burhave K., et al. Sulfasalazine and its anti-inflammatory metabolite 5-aminosalicylic acid: Effect on arachidonic acid metabolism in human neutrophils and free radical scavenging. Prostaglandins, Thomboxane and Leukotriene Research 17: 9-8-922; 1999.

37. Papadakis K. A., Targan S. R. Current theories on the causes of inflammatory bowel disease. Gastroenterol Clin North Am 28: 323-351; 1999.

38. Stein R. B., Hanauer S. B. Medical therapy for inflammatory bowel disease. Gastroenterol Clin North Am 28: 297-321; 1999.

39. Hanauer S. B., Meyers S., Sachar D. B. The pharmacology of anti-inflammatory drugs in inflammatory bowel disease. In Kirsner J. B., Shorter R. G. (eds) Inflammatory Bowel Disease, ed 4. Baltimore, Williams & Wilkins pp. 643-663, 1995.

40. Emerit J. S., Pelletier S., Likforman J., et al. Phase II trial of copper zinc superoxide dismutase (Cu, Zn, SOD) in the treatment of Crohn's disease. Free Radic Res Common 12: 563-596; 1991.

What is claimed is:

1. A method of treating an inflammatory bowel disease in a mammal by reducing cytokine gene expression in colonic tissue of the mammal, the method comprising
administering to the mammal by rectal delivery to a colon of the mammal a therapeutically-effective amount of 5-aminosalicylic acid or a pharmaceutically-acceptable salt thereof, and a therapeutically-effective amount of N-acetylcysteine or a pharmaceutically-acceptable salt thereof, whereby administration of the combination of 5-aminosalicylic acid, or a pharmaceutically-acceptable salt thereof, and N-acetylcysteine, or a pharmaceutically-acceptable salt thereof, causes reduced cytokine gene expression in colonic tissue of the mammal.

2. The method of claim 1, wherein the cytokine is selected from the group consisting of IL 1a, IL 1b, IL-4, IL-6, and TNFα.

3. The method of claim 1, wherein the 5-aminosalicylic acid or a pharmaceutically-acceptable salt thereof, and the N-acetylcysteine or a pharmaceutically-acceptable salt thereof, are together disposed in a pharmaceutically acceptable carrier.

4. The method of claim 1, wherein the 5-aminosalicylic acid or a pharmaceutically-acceptable salt thereof, and the N-acetylcysteine or a pharmaceutically-acceptable salt thereof, are administered separately.

5. The method of claim 1, wherein macroscopic injury or inflammation to colonic mucosa of the mammal is reduced.

6. The method of claim 1, wherein microscopic injury to colonic mucosa of the mammal is reduced.

7. The method of claim 1, wherein the mammal is a human.

8. A method of treating an inflammatory bowel disease in a mammal by reducing myeloperoxidase activity in colonic tissue of the mammal, the method comprising
administering to the mammal by rectal delivery to a colon of the mammal a therapeutically-effective amount of 5-aminosalicylic acid or a pharmaceutically-acceptable salt thereof, and a therapeutically-effective amount of N-acetylcysteine or a pharmaceutically-acceptable salt thereof, whereby administration of the combination of 5-aminosalicylic acid, or a pharmaceutically-acceptable salt thereof, and N-acetylcysteine, or a pharmaceutically-acceptable salt thereof, causes reduced myeloperoxidase activity in colonic tissue of the mammal.

9. The method of claim 8, wherein the 5-aminosalicylic acid or a pharmaceutically-acceptable salt thereof, and the N-acetylcysteine or a pharmaceutically-acceptable salt thereof, are together disposed in a pharmaceutically acceptable carrier.

10. The method of claim 8, wherein the 5-aminosalicylic acid or a pharmaceutically-acceptable salt thereof, and the N-acetylcysteine or a pharmaceutically-acceptable salt thereof, are administered separately.

11. The method of claim 8, wherein macroscopic injury or inflammation to colonic mucosa of the mammal is reduced.

12. A method of treating an inflammatory bowel disease in a mammal, comprising:
contacting a colonic cell of the mammal with a therapeutically-effective amount of 5-aminosalicylic acid or a pharmaceutically-acceptable salt thereof, and a therapeutically-effective amount of N-acetylcysteine or a pharmaceutically-acceptable salt thereof.

13. The method of claim 12, wherein macroscopic injury to colonic mucosa of the mammal is reduced.

14. The method of claim 12, wherein inflammation in colonic mucosa of the mammal is reduced.

15. A method of treating an inflammatory bowel disease in a mammal by reducing cytokine gene expression in colonic tissue of the mammal, the method comprising
contacting a colonic cell of the mammal with a therapeutically-effective amount of 5-aminosalicylic acid or a pharmaceutically-acceptable salt thereof, and a therapeutically-effective amount of N-acetylcysteine or a pharmaceutically-acceptable salt thereof, whereby the combination of 5-aminosalicylic acid, or a pharmaceutically-acceptable salt thereof, and N-acetylcysteine, or a pharmaceutically-acceptable salt thereof, causes reduced cytokine gene expression in the cell.

16. The method of claim 15, wherein the cytokine is selected from the group consisting of IL 1a, IL 1b, IL-4, IL-6, and TNFα.

17. The method of claim 15, wherein macroscopic injury or inflammation to colonic mucosa of the mammal is reduced.

18. A method of treating an inflammatory bowel disease in a mammal by reducing myeloperoxidase activity in colonic tissue of the mammal, the method comprising
contacting a colonic cell of the mammal with a therapeutically-effective amount of 5-aminosalicylic acid or a pharmaceutically-acceptable salt thereof, and a therapeutically-effective amount of N-acetylcysteine or a pharmaceutically-acceptable salt thereof, whereby the combination of 5-aminosalicylic acid, or a pharmaceutically-acceptable salt thereof, and N-acetylcysteine, or a pharmaceutically-acceptable salt thereof, causes reduced myeloperoxidase activity in the cell.

19. The method of claim 18, wherein macroscopic injury or inflammation to colonic mucosa of the mammal is reduced.

* * * * *